(12) United States Patent
Yaron et al.

(10) Patent No.: US 8,149,270 B1
(45) Date of Patent: Apr. 3, 2012

(54) HIGH RESOLUTION ENDOSCOPE

(75) Inventors: Avi Yaron, Tenafly, NJ (US); Mark Schechterman, Nes-Ziona (IL)

(73) Assignee: Visionsense Ltd., Petah Tikva (IL)

( * ) Notice: Subject to any disclaimer, the term of this patent is extended or adjusted under 35 U.S.C. 154(b) by 1141 days.

(21) Appl. No.: 11/958,211

(22) Filed: Dec. 17, 2007

Related U.S. Application Data

(60) Provisional application No. 60/875,673, filed on Dec. 18, 2006.

(51) Int. Cl.
*H04N 13/00* (2006.01)

(52) U.S. Cl. .......................... 348/45; 348/46
(58) Field of Classification Search .......... None
See application file for complete search history.

(56) References Cited

U.S. PATENT DOCUMENTS

| | | | |
|---|---|---|---|
| 4,873,572 A * | 10/1989 | Miyazaki et al. | 348/45 |
| 6,306,082 B1 | 10/2001 | Takahashi et al. | |
| 6,704,043 B2 * | 3/2004 | Goldstein et al. | 348/45 |
| 6,817,975 B1 | 11/2004 | Farr et al. | |
| 7,290,880 B1 * | 11/2007 | Yaron et al. | 351/206 |
| 2002/0141057 A1 | 10/2002 | Weissman et al. | |
| 2002/0188172 A1 | 12/2002 | Irion et al. | |

* cited by examiner

*Primary Examiner* — John B. Walsh
(74) *Attorney, Agent, or Firm* — Merchant & Gould P.C.

(57) ABSTRACT

A stereoscopic endoscope employing a single light sensor array and a lenticular lens layer located at a proximal end of the endoscope, a pair of periscopic prisms located at a distal end of the endoscope and an optical relay assembly array located between the pair of periscopic prisms and the light sensor array. One prism of the pair of periscopic prisms receives a right view of an object and another prism of the pair receives a left view of the object. The interpupilar distance (IPD) between the right and left view is substantially large, thereby increasing the resolution of a stereoscopic image which is eventually displayed on a display. Another embodiment includes a set of three light sensor arrays, a light director and three lenticular lens layers. Each light sensor array detects light at a predetermined range of wavelengths (e.g. red, green and blue).

14 Claims, 9 Drawing Sheets

HIGH RESOLUTION ENDOSCOPE

FIELD OF THE DISCLOSED TECHNIQUE

The disclosed technique relates to endoscopes in general, and to methods and systems for providing a high resolution image of an object, in particular.

BACKGROUND OF THE DISCLOSED TECHNIQUE

Endoscopes are used in the medical field, for imaging the inner wall of a lumen of the body of a patient (e.g., colon, ureter), as well as providing the surgeon a view of an internal region of the body during a minimal invasive surgery (MIS), such as laparoscopy and brain surgery. A display can display the image of an object picked up by the endoscope, either as a two-dimensional image, or a set of the right view and the left view of the object, in which case the surgeon can perceive a stereoscopic perception of the object, by using stereoscopic spectacles. The stereoscopic perception provides depth to the image, as if the surgeon was viewing the object with naked eyes, thereby aiding the surgeon to perform a more successful operation.

Stereoscopic endoscopes are known in the art. Such endoscopes generally include an optical assembly at the tip thereof, to pick up light beams respective of a right view and a left view of the object. The endoscope further includes two image detectors, such as charge-coupled device (CCD), to detect a right image and a left image of the object, according to the light beams which the optical assembly projects on the respective CCD. The CCD's are connected to a processor which produces the right image and the left image according to the output of the CCD's, and directs a display to display the right image and the left image.

The small diameter of the endoscope restricts the size of the optical elements, such as optical assembly, objective and CCD, which are assembled within the endoscope, thereby limiting the resolution of the final image. Much effort has been expended in order to increase the resolution of the image which the display displays. One way to increase the resolution, is by employing a CCD having greater number of cells. To that end, the CCD is mounted at the proximal end of the endoscope, where ample room is available, and light is transmitted to the CCD from the tip thereof, by employing a relay lens system. Another avenue is employment of two set of CCD's, each set including three CCD's, one for each of the red, green, and blue colors.

U.S. Pat. No. 6,306,082 B1 issued to Takahashi et al., and entitled "Stereoendoscope wherein Images Having Passed Through Plural Incident Pupils are Transmitted by Common Relay Optical Systems", is directed to an endoscope which employs a series of relay lenses to project two images of an object on a single image taking device, including a lenticular lens in front of the image taking device. The endoscope includes two objective optical systems, a relay lens system, an image taking device, a lenticular lens, a light source apparatus, a camera control unit (CCU), a scan converter, a color monitor, and shutter spectacles.

The two objective optical systems are identical and each of them is made of optical lenses of the same characteristics. The light source apparatus is connected to the distal end of the endoscope, by a light guide. The CCU is connected to the image taking device and to the scan converter. The scan converter is connected to the color monitor. The two objective optical systems are located at a distal end of the endoscope. The relay lens system is located between the two objective optical systems and the image taking device. The lenticular lens is located in front of the image taking device. The image taking device is located in a gripped section of the endoscope, at a proximal end of the endoscope.

The two objective optical systems form a right image and a left image of an object, at a parallax from each other, and transmit the right and left images to the relay lens system. The relay lens system multiple-transmits the right and left images to image taking device. The lenticular lens forms the right and left images at intervals of one row or one line, on the image taking device. The CCU processes the signals received from the image taking device, the scan converter converts the signal from the CCU to a video signal, and the monitor displays the video signal. The shutter spectacles enable a user to view a stereoscopic image of the object.

U.S. Pat. No. 6,817,975 B1 issued to Farr et al., and entitled "Endoscope" is directed to an endoscope having an objective, a relay lens system, an ocular lens system and a camera. The objective is located at a distal end of the endoscope. The ocular lens system is located at a proximal end of the endoscope. The relay lens system is located between the objective and the ocular lens system. The camera is located behind the ocular lens system. The objective is constructed such that a first intermediate image of an object, falls within the glass portion of the most proximal portion of the objective lens, in close proximity to the distal end of the relay lens system.

U.S. Pat. No. 6,624,935 B2 issued to Weissman et al., and entitled "Single-Axis Stereoscopic Video Imaging System with Centering Capability", is directed to a stereoscopic imaging system. The stereoscopic imaging system includes a single axis optical system, an electronic shutter, an aperture and a single or multiple sensor imaging device. The single axis imaging system is a video lens, photographic lens, microscope, telescope or endoscope. The electronic shutter is a device which is electronically controlled to alternately block the transmission of light. The electronic shutter is a liquid crystal device. Alternatively, the electronic shutter is a polarization selector.

The aperture is located behind the single axis optical system. The electronic shutter is located between the single axis optical system and the aperture. The single or multiple sensor imaging device is located behind the aperture. The electronic shutter alternately blocks a right view and a left view of a target. The right view and the left view are presented to the single or multiple sensor imaging device for viewing the right view and the left view of the target stereoscopically.

U.S. Pat. No. 6,832,985 B2 issued to Irion et al., and entitled "Endoscopic System with Instrument Position and Orientation Display", is directed to an endoscopic system for displaying information respective of the position and orientation of an instrument, as well as an image detected by an endoscope. The endoscopic system includes an endoscope, a video unit, a monitor, an assessment and control unit, and a position sensing device. The endoscope includes an endoscope objective and a relay lens system. The instrument serves to perform an operation such as diagnosis or therapeutical treatment. The assessment and control unit is a video processor unit.

The endoscope objective is located at a distal end of the endoscope. The video unit is located at a proximal end of the endoscope. The position sensing device is attached to the instrument. The relay lens system transmits an image detected by the endoscope objective, to the video unit. The endoscope objective is focused on an image plane of an object and is associated with a respective coverage field cone. The assessment and control unit is connected to the position sensing device and to the monitor. The position sensing device sends a signal respective of the orientation of the instrument relative to the coverage field cone, to the assessment and control unit. The monitor displays a symbol indicating the orientation of the instrument, in addition to an image detected by the endoscope.

Reference is now made to FIG. 1, which is a schematic illustration of an endoscope generally referenced 1, as known in the art. Endoscope 1 includes an elongated endoscopic housing 2, a right prism 4, a left prism 6, an aperture stop 8, an objective 10, a lenticular lens layer 12 and a light sensor array 14. Aperture stop 8 includes a right pupil 16 and a left pupil 18. Right prism 4 and left prism 6 are located in front of right pupil 16 and left pupil 18, respectively. Objective 10 is located behind aperture stop 8. Lenticular lens layer 12 is located between objective 10 and light sensor array 14. A processor 20 is connected with light sensor array 14 and with a display 22. Right prism 4, left prim 6, aperture stop 8, objective 10, lenticular lens layer 12 and light sensor array 14 are located at a distal end of elongated endoscopic housing 2.

Endoscope 1 is inserted into a body cavity 24 of a patient (not shown), in order to detect an image of an object 26. Object 26 is located in front of right prism 4 and left prism 6. Right prism 4 receives a light beam 28A respective of a right view of object 26. Left prism 6 receives a light beam 30A respective of a left view of object 26. Light beam 28A reflects within right prism 4, passes through right pupil 16 and objective 10, to strike a lenticular lens 32 of lenticular lens layer 12, as a light beam 28B. Light beam 30A reflects within left prism 6, passes through left pupil 18 and objective 10, to strike lenticular lens 32 as a light beam 30B. Lenticular lens 32 separates light beams 28B and 30B, and directs light beams 28B and 30B to adjacent cells $34_R$ and $34_L$ of light sensor array 14, respectively.

Processor 20 produces a video output respective of the right view and left view of object 26, according to an output of light sensor array 14, for display 22 to display a right image and a left image of object 26. A user can perceive a stereoscopic sensation of object 26, by viewing display 22 via a stereoscopic pair of spectacles (not shown).

Reference is now made to FIG. 2, which is a schematic illustration of an endoscope generally referenced 40, as known in the art. Endoscope 40 includes an elongated endoscopic housing 42, a front aperture stop 44, an objective 46, an optical relay assembly array 48, a rear aperture stop 50, a front right lens $52_{1R}$, a front left lens $52_{1L}$, a rear right lens $52_{2R}$, a rear left lens $52_{2L}$, a right light sensor array $54_R$, and a left light sensor array $54_L$. Front aperture stop 44 includes a front right pupil $56_R$ and a front left pupil $56_L$. Optical relay assembly array 48 includes a plurality of optical relay assemblies $58_1$ and $58_2$. Rear aperture stop 50 includes a rear right pupil $60_R$ and a rear left pupil $60_L$.

An object 62 is located within a body cavity 64 of a patient (not shown). Front aperture stop 44 is located between object 62 and objective 46. Optical relay assembly array 48 is located between objective 46 and rear aperture stop 50. Front right lens $52_{1R}$ and front left lens $52_{1L}$ are located in front of rear right pupil $60_R$ and rear left pupil $60_L$, respectively. Rear right lens $52_{2R}$ and rear left lens $52_{2L}$ are located behind rear right pupil $60_R$ and rear left pupil $60_L$, respectively. Right light sensor array $54_R$ and left light sensor array $54_L$ are located behind rear right lens $52_{2R}$ and rear left lens $52_{2L}$, respectively. Front aperture stop 44, objective 46, optical relay assembly array 48, rear aperture stop 50, front right lens $52_{1R}$, front left lens $52_{1L}$, rear right lens $52_{2R}$, rear left lens $52_{2L}$, right light sensor array $54_R$, and left light sensor array $54_L$ are located within elongated endoscopic housing 42. A processor 66 is connected with right light sensor array $54_R$, left light sensor array $54_L$, and with a display 68.

Objective 46 receives light beams 70A and 72A, respective of a right view and a left view, respectively of object 62, through front right pupil $56_R$ and front left pupil $56_L$, respectively. Objective 46 projects a right image $74_R$ and a left image $74_L$ of object 62, according to light beams 70B and 72B, respectively, on a front image plane (not shown) of optical relay assembly $48_1$. There is a disparity δ between right image $74_R$ and left image $74_L$. Optical relay assembly array 48 transmits light beams 70B and 72B there through, in a multiple manner, to project a right image $76_R$ and a left image $76_L$ of object 62, on a rear image plane (not shown) of optical relay assembly $48_2$, according to light beams 70C and 72C, respectively. There is the same disparity δ between right image $76_R$ and left image $76_L$.

Front right lens $52_{1R}$ transmits right image $76_R$ to rear right lens $52_{2R}$, through rear right pupil $60_R$. Front left lens $52_{1L}$ transmits left image $76_L$ to rear left lens $52_{2L}$, through rear left pupil $60_L$. Rear right lens $52_{2R}$ projects a light beam 70D respective of the right view of object 62, on right light sensor array $54_R$. Rear left lens $52_{2L}$ projects a light beam 72D respective of the left view of object 62, on left light sensor array $54_L$. Processor 66 produces a video output respective of the right view and left view of object 62, according to an output of right light sensor arrays $54_R$ and left light sensor array $54_L$, for display 68 to display a right image and a left image of object 62. A user can perceive a stereoscopic sensation of object 62, by viewing display 68 via a stereoscopic pair of spectacles (not shown).

Reference is now made to FIGS. 3A, and 3B. FIG. 3A is a schematic illustration of an endoscope generally referenced 100, as known in the art. FIG. 3B is a schematic illustration of each of the right image detector assembly and the left image detector assembly, of the endoscope of FIG. 3A.

With reference to FIG. 3A, endoscope 100 includes an elongated endoscopic housing 102, a front aperture stop 104, an objective 106, an optical relay assembly array 108, a rear aperture stop 110, a front right lens $112_{1R}$, a front left lens $112_{1L}$, a rear right lens $112_{2R}$, a rear left lens $112_{2L}$, a right image detector assembly $114_R$, and a left image detector assembly $114_L$. Front aperture stop 104 includes a front right pupil $116_R$ and a front left pupil $116_L$. Optical relay assembly array 108 includes a plurality of optical relay assemblies $118_1$ and $118_2$. Rear aperture stop 110 includes a rear right pupil $120_R$ and a rear left pupil $120_L$.

An object 122 is located within a body cavity 124 of a patient (not shown). Front aperture stop 104 is located between object 122 and objective 106. Optical relay assembly array 108 is located between objective 106 and rear aperture stop 110. Front right lens $112_{1R}$ and front left lens $112_{1L}$ are located in front of rear right pupil $120_R$ and rear left pupil $120_L$, respectively. Rear right lens $112_{2R}$ and rear left lens $112_{2L}$ are located behind rear right pupil $120_R$ and rear left pupil $120_L$, respectively. Right image detector assembly $114_R$ and left image detector assembly $114_L$ are located behind rear right lens $112_{2R}$ and rear left lens $112_{2L}$, respectively. Front aperture stop 104, objective 106, optical relay assembly array 108, rear aperture stop 110, front right lens $112_{1R}$, front left lens $112_{1L}$, rear right lens $112_{2R}$, rear left lens $112_{2L}$, right image detector assembly $114_R$ and left image detector assembly $114_L$ are located within elongated endoscopic housing 102. A processor 126 is connected with right image detector assembly $114_R$, left image detector assembly $114_L$, and with a display 128.

With reference to FIG. 3B, an image detector assembly 150, includes three prisms 152, 154, and 156, and three light sensor arrays $158_R$, $158_G$, and $158_B$. Light sensor array $158_R$ detects an image (not shown) in a red range of wavelengths. Light sensor array $158_G$ detects the image in a green range of wavelengths. Light sensor array $158_B$ detects the image in a blue range of wavelengths. A first surface 160 of prism 154 makes contact with a surface 162 of prism 152. A second surface 164 of prism 154 makes contact with a surface 166 of prism 156. Light sensor array $158_R$ is located behind a surface 168 of prism 152. Light sensor array $158_G$ is located behind a surface 170 of prism 154. Light sensor array $158_B$ is located behind a surface 172 of prism 156. Processor 126 is connected with light sensor arrays $158_R$, $158_G$, and $158_B$.

A portion of a light beam 174A reflects from surface 162 as a light beam 174B and strikes light sensor array $158_R$. Another portion of light beam 174A passes through prisms 152, 154, and 156, to strike light sensor array $158_B$ as a light beam 174B. A further portion of light beam 174A passes through prism 152, and reflects from surface 164, as a light beam 174C, to strike light sensor array $158_G$. In this manner, light sensor arrays $158_R$, $158_G$, and $158_B$, detect an image (not shown) of an object (not shown), in a red, a green, and a blue range of wavelengths, respectively.

With reference back to FIG. 3A, right image detector assembly $114_R$ receives a light beam 176 respective of a right view image $178_R$, of object 122, via rear right lens $112_{2R}$, similar to the manner light sensor array $54_R$ (FIG. 2) receives light beam 70D respective of right image $74_R$ of object 62, via rear right lens $52_{2R}$. Left image detector assembly $114_L$ receives a light beam 180 respective of a left view image $178_L$, of object 122, via rear left lens $112_{2L}$, similar to the manner light sensor array $54_L$ receives light beam 72D respective of left image $74_L$ of object 62, via rear left lens $52_{2L}$.

Processor 126 produces a color video output respective of the right view and left view of object 122, according to an output of right image detector assembly $114_R$ and left image detector assembly $114_L$, for display 128 to display a right color image and a left color image of object 122. A user can perceive a stereoscopic sensation of object 122, in color, by viewing display 128 via a stereoscopic pair of spectacles (not shown).

SUMMARY OF THE DISCLOSED TECHNIQUE

It is an object of the disclosed technique to provide a novel method and system for producing a high resolution stereoscopic image by an endoscope.

In accordance with the disclosed technique, there is thus provided a stereoscopic endoscope. The stereoscopic endoscope includes an elongated endoscopic housing, an interpupilar distance (IPD) transformer, an objective, an optical relay assembly array, a light sensor array, a lenticular lens layer, and an optical assembly. The IPD transformer is located at a distal end of the elongated endoscopic housing and behind an object. The IPD transformer receives light beams respective of a right view and a left view of the object, at a substantially large IPD. The objective is located behind the IPD transformer. The objective receives the light beams from the IPD transformer.

The objective projects a distal right view image and a distal left view image of the object on a distal image plane. The distal image plane is located in the vicinity of the distal end. The optical relay assembly array is located behind the objective. The objective is optically coupled with the optical relay assembly array. The optical relay assembly array includes a plurality of serially located optical relay assemblies. The optical relay assemblies sequentially relay the distal right view image and the distal left view image. A proximal optical relay assembly of the optical relay assembly array is located at a proximal end of the elongated endoscopic housing. The proximal optical relay assembly projects a relayed right view image and a relayed left view image of the object, on a proximal image plane located at the proximal end.

The light sensor array is located behind the optical relay assembly array. The light sensor array includes a plurality of light sensors. The lenticular lens layer is located in front of the light sensor array. The lenticular lens layer includes a plurality of lenticular elements. Each of the lenticular elements is located in front of a selected two-dimensional group of the light sensors.

The optical assembly is located in front of the lenticular lens layer. The optical assembly transmits a relayed right view light beam according to the relayed right view image, to a respective one of the lenticular elements. The optical assembly further transmits a relayed left view light beam according to the relayed left view image, to the respective lenticular element. The respective lenticular element transmits the relayed right view light beam and the relayed left view light beam, to respective ones of the selected group of the light sensors. This is to enable respective ones of the selected group of the light sensors, to produce a sensor output respective of the relayed right view light beam and the relayed left view light beam.

In accordance with another aspect of the disclosed technique, there is thus provided a stereoscopic endoscope. The stereoscopic endoscope includes an elongated endoscopic housing, an interpupilar distance (IPD) transformer, an objective, an optical relay assembly array, a light detector assembly, and an optical assembly. The light detector assembly includes a set of three light sensor arrays, a set of three lenticular lens layers, and a light director.

The IPD transformer is located at a distal end of the elongated endoscopic housing and behind an object. The IPD transformer receives light beams respective of a right view and a left view of the object, at a substantially large IPD. The objective is located behind the IPD transformer. The objective receives the light beams from the IPD transformer. The objective projects a distal right view image and a distal left view image of the object, on a distal image plane. The distal image plane is located at the distal end.

The optical relay assembly array is located behind the objective. The optical relay assembly array includes a plurality of serially located optical relay assemblies. The optical relay assemblies sequentially relay the distal right view image and the distal left view image. A proximal optical relay assembly of the optical relay assembly array, is located at a proximal end of the elongated endoscopic housing. The proximal optical relay assembly projects a relayed right view image and a relayed left view image of the object, on a proximal image plane located at the proximal end.

The light detector assembly is located behind the optical relay assembly array. Each of the set of three light sensor arrays is optically coupled with the optical relay assembly array. Each of the set of three light sensor arrays includes a plurality of light sensors. Each of the set of three lenticular lens layers is located in front of a respective one of the set of three light sensor arrays. Each of the set of three lenticular lens layers includes a plurality of lenticular elements. Each of the lenticular elements is located in front of a respective two-dimensional group of the light sensors of the respective light sensor array.

The light director is optically coupled with the optical relay assembly array and with the set of three lenticular lens layers. The light director directs incoming light to predetermined directions, in predetermined ranges of wavelengths, toward predetermined lenticular elements of each lenticular lens layer of the set of three lenticular lens layers.

The optical assembly is located between the optical relay assembly array and the light director. The optical assembly transmits a relayed right view light beam to the light director, according to the relayed right view image. The optical assembly further transmits a relayed left view light beam to the light director, according to the relayed left view image. The light director directs each of the relayed right view light beam and the relayed left view light beam, toward each of the predetermined lenticular elements. Each of the predetermined lenticular elements transmits the relayed right view light beam and the relayed left view light beam, to the respective group of the light sensors. This is to enable the respective group of each of the set of three light sensor arrays, to produce a corresponding sensor output respective of the relayed right view light beam and the relayed left view light beam.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
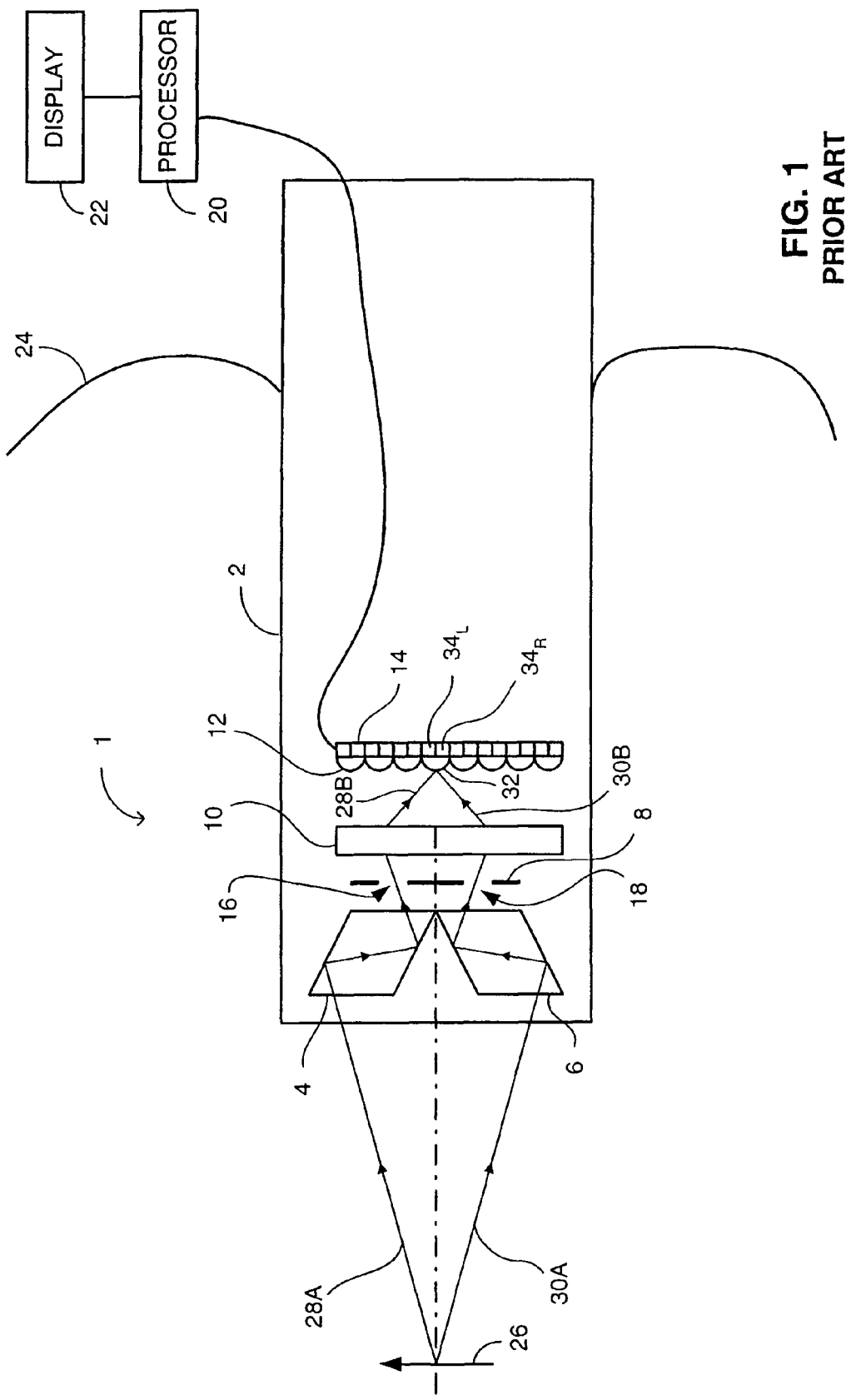
FIG. 1 is a schematic illustration of an endoscope as known in the art.
Figure 2:
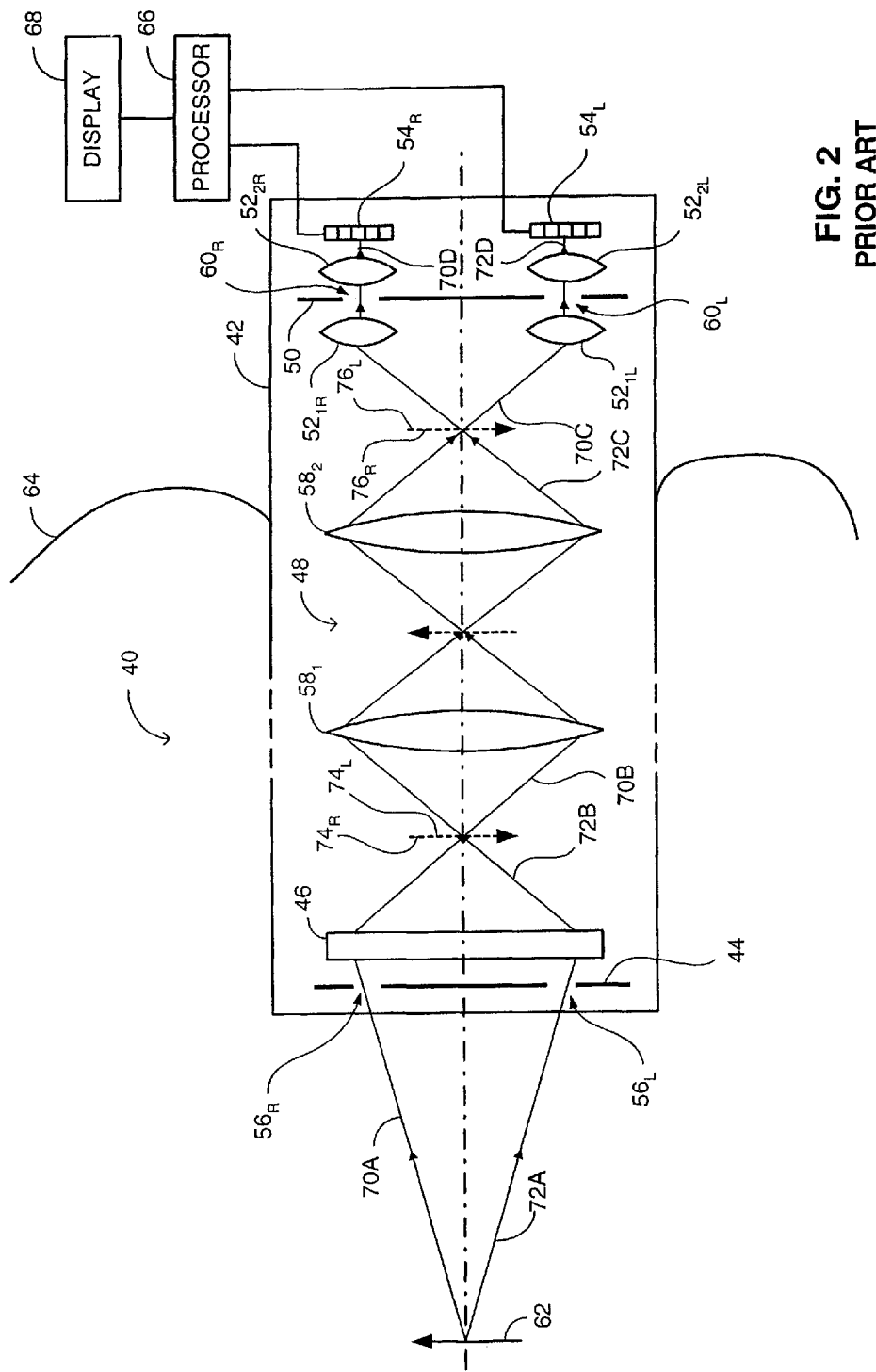
FIG. 2 is a schematic illustration of an endoscope as known in the art.
Figure 3A:
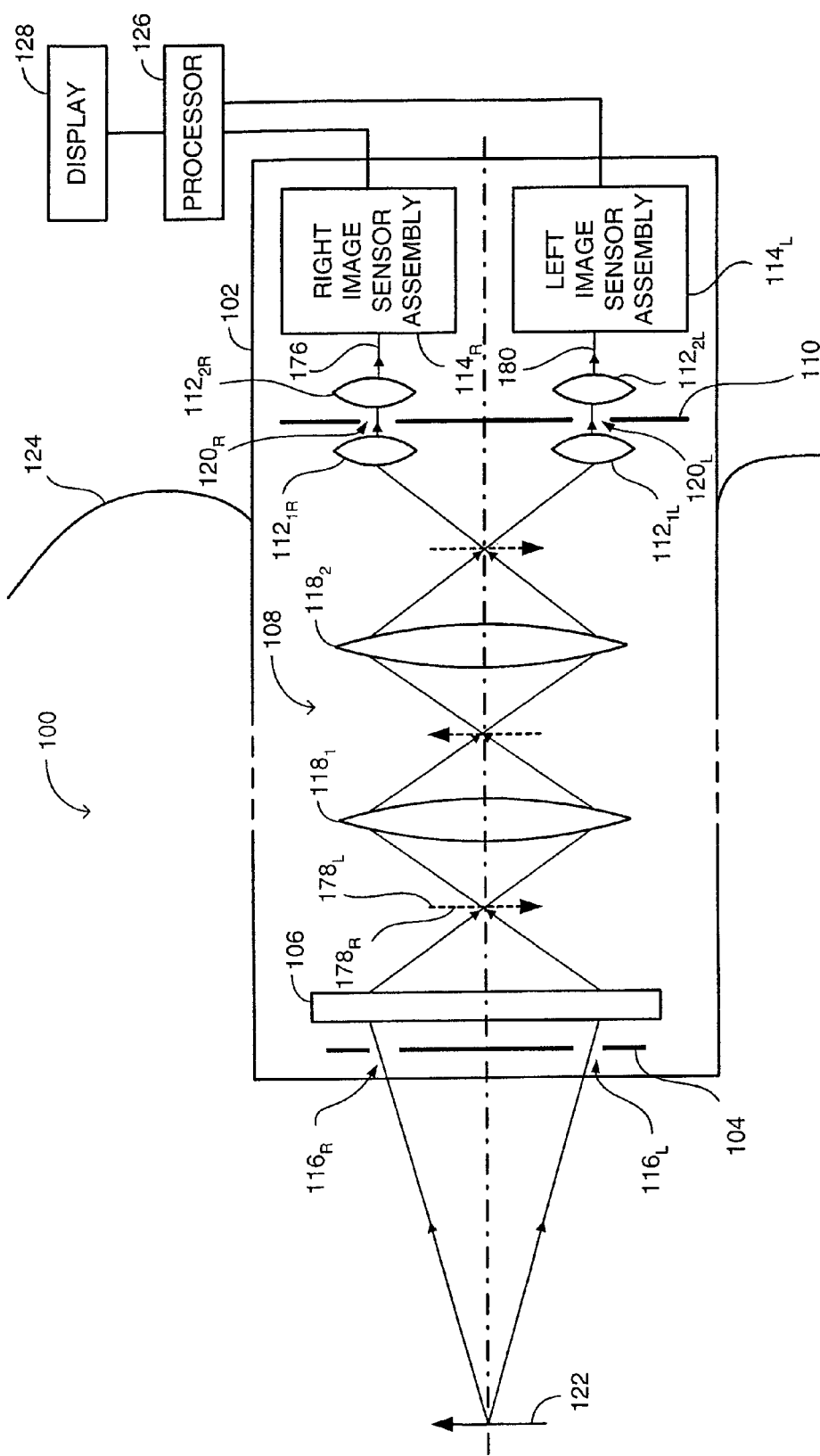
FIG. 3A is a schematic illustration of an endoscope as known in the art.
Figure 3B:
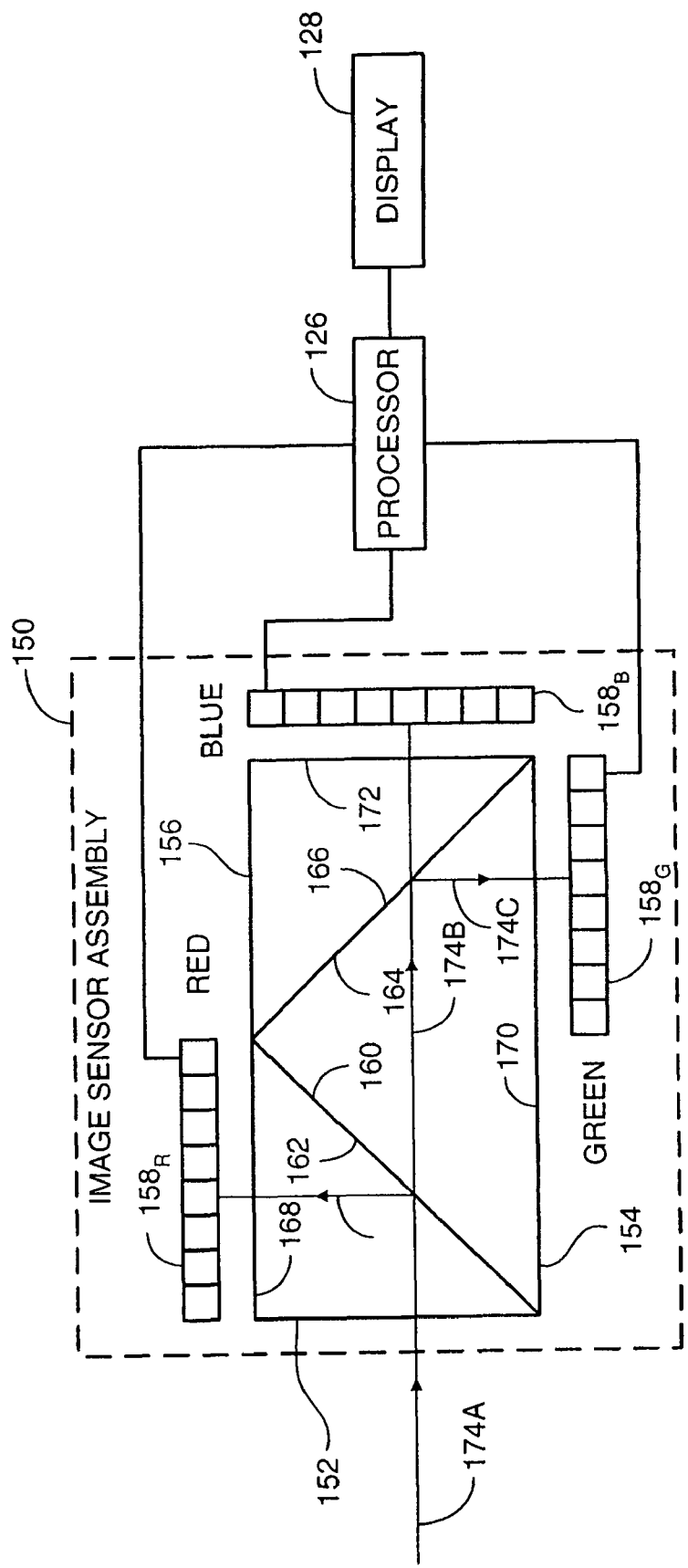
FIG. 3B is a schematic illustration of each of the right image detector assembly and the left image detector assembly, of the endoscope of FIG. 3A.

The disclosed technique overcomes the disadvantages of the prior art by employing a single light sensor array and a lenticular lens layer located at a proximal end of an endoscope, a pair of periscopic prisms located at a distal end of the endoscope, and an optical relay assembly array located between the pair of periscopic prisms and the light sensor array. One prism of the pair of periscopic prisms receives a right view of an object, and another prism of the pair of the periscopic prisms receives a left view of the object. Due to the nature of the pair of periscopic prisms, the interpupilar distance (IPD) between the right view and the left view is substantially large, thereby increasing the resolution of a stereoscopic image which is eventually displayed on a display. The pair of periscopic prisms transmit light beams respective of the right view and the left view of the object, to the optical relay assembly array, at a reduced IPD, thereby allowing usage of a substantially low gage and low weight optical relay assembly array. Furthermore, placing the light sensor array at the proximal end of the endoscope, where ample room is available, allows usage of a substantially large light sensor array, having a substantially large number of cells, thereby enabling production of a substantially high resolution stereoscopic image of the object.

According to another aspect of the disclosed technique, the endoscope includes a set of three light sensor arrays, a light director, and three lenticular lens layers, instead of a single light sensor array and a single lenticular lens layer. Each lenticular lens layer is located in front of a respective light sensor array. Each light sensor array detects light at a predetermined range of wavelengths (e.g., red, green, and blue). The light director separates each of the light beams respective of the right view and the left view of the object, according to a plurality of predetermined ranges of wavelengths, and directs these separated light beams in predetermined directions toward each of the light sensor arrays. The lenticular lens layer associated with the respective light sensor array, projects light beams respective of the right view and the left view, to adjacent cells of the respective light sensor array. Each light sensor array produces an output respective of the right view and the left view of the object, in a different color. A processor can direct a display to display a stereoscopic color image of the object, according to these outputs. Since only a single set of three light sensor arrays is placed at the proximal end of the endoscope, where ample room is available, substantially large light sensor arrays can be employed, thereby enabling production of a substantially high resolution color stereoscopic image.

The term "interpupilar distance (IPD) transformer" herein below, refers to an optical device which enables an optical relay assembly array to receive light beams respective of a right view image and a left view image of an object, at an IPD which is larger than the one that can be provided to the optical relay assembly array, without the IPD transformer. This substantially large IPD enables the light sensor array to enhance the stereoscopic characteristics of the image produced thereby. For this purpose, IPD transformer can include for example, a pair of periscopic prisms, and the like.

Figure 4:
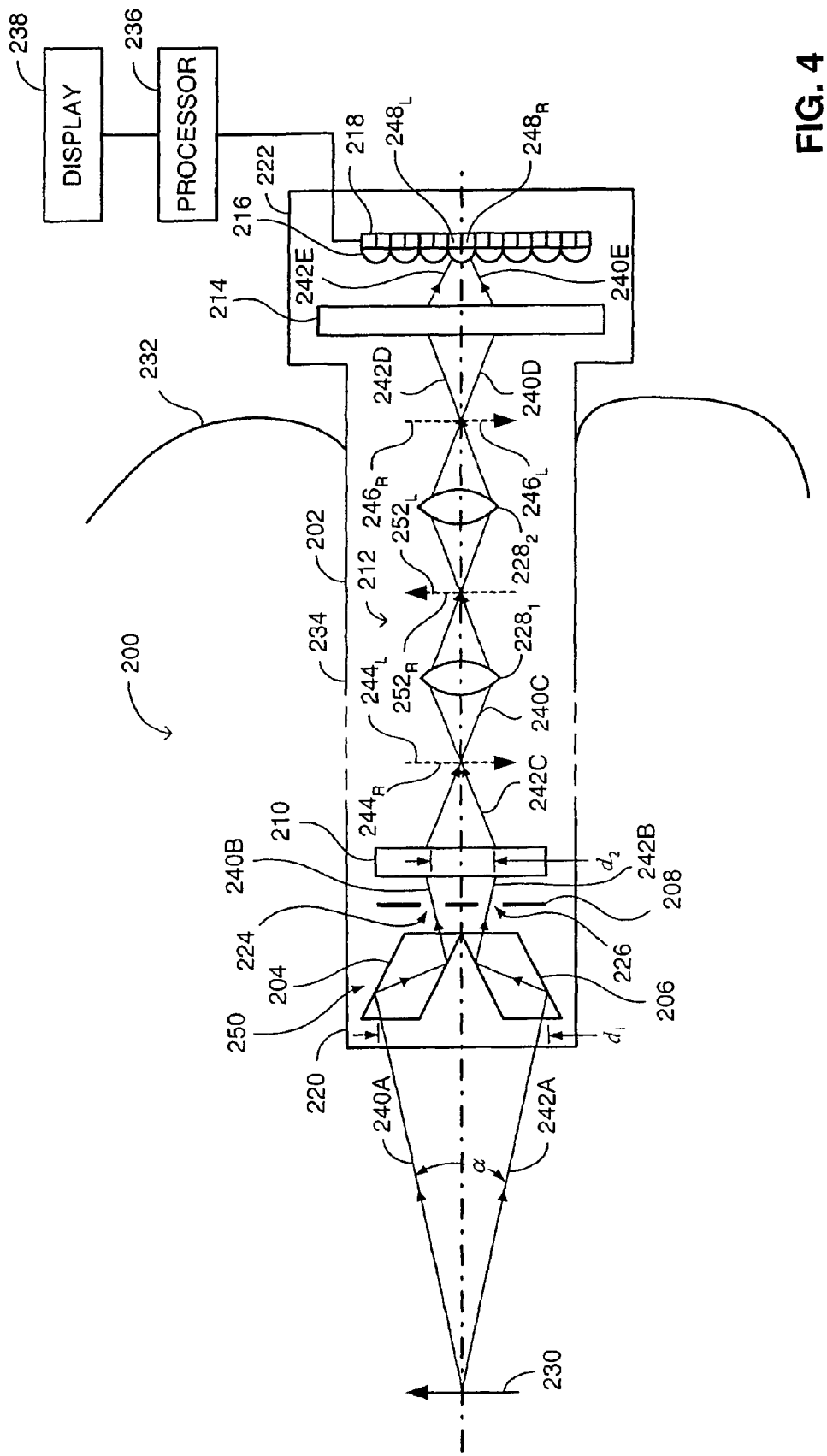
FIG. 4 is a schematic illustration of an endoscope, constructed and operative in accordance with an embodiment of the disclosed technique.

Reference is now made to FIG. 4, which is a schematic illustration of an endoscope, generally referenced 200, constructed and operative in accordance with an embodiment of the disclosed technique. Endoscope 200 includes an elongated endoscopic housing 202, an IPD transformer 250, an aperture stop 208, an objective 210, a optical relay assembly array 212, an optical assembly 214, a lenticular lens layer 216 and a light sensor array 218. Elongated endoscopic housing 202 includes a distal end 220 and a proximal end 222. IPD transformer 250 includes a right periscopic prism 204 and a left periscopic prism 206. Aperture stop 208 includes a right pupil 224 and a left pupil 226. Optical relay assembly array 212 includes a plurality of optical relay assemblies $228_1$ and $228_2$. Elongated endoscopic housing 202 is made of a rigid material. Light sensor array 218 is a solid state light detector made of a semiconductor such as silicon, Gallium Arsenide (GaAs), and the like, in form of a charged-coupled device (CCD), complementary metal oxide silicon (CMOS), and the like.

An object 230 is located within a cavity 232 of the body of a patient (not shown). Right periscopic prism 204, left periscopic prism 206, aperture stop 208, and objective 210 are located at distal end 220. Optical assembly 214, lenticular lens layer 216, and light sensor array 218 are located at proximal end 222. Lenticular lens layer 216 is located in front of light sensor array 218. Optical relay assembly array 212 is located in a midsection 234 of endoscope 200, between distal end 220 and proximal end 222.

Object 230 is located in front of right periscopic prism 204 and left periscopic prism 206. Aperture stop 208 is located between right periscopic prism 204 and left periscopic prism 206 on one hand, and objective 210 on the other. Optical relay assembly array 212 is located between objective 210 and optical assembly 214. Lenticular lens layer 216 is located between optical assembly 214 and light sensor array 218. A processor 236 is coupled with light sensor array 218 and with a display 238. Display 238 can be a cathode ray tube (CRT) display, autostereoscopic display, head-mounted retinal display, volumetric display, multi-LCD (liquid crystal display) display, and the like.

Right periscopic prism 204 receives a light beam 240A respective of a right view of object 230. Left periscopic prism 206 receives a light beam 242A respective of a left view of object 230. An angle of introversion between light beams 240A and 242A is designated by α. An IPD respective of the pair of right periscopic prism 204 and left periscopic prism 206 is designated by $d_1$. Right periscopic prism 204 reflects light beam 240A toward objective 210, as a light beam 240B, via right pupil 224. Left periscopic prism 206 reflects light beam 242A toward objective 210, as a light beam 242B, via left pupil 226. An IPD respective of right pupil 224 and left pupil 226 is designated by $d_2$, where $d_2 < d_1$.

Objective 210 projects a right image $244_R$ and a left image $244_L$ of object 230, according to light beams 240C and 242C, respectively, on a front image plane (not shown) of optical relay assembly $228_1$. There is a disparity δ between right image $244_R$ and left image $244_L$. Optical relay assembly array 212 transmits light beams 240C and 242C there through, in a multiple manner, to project a right image $246_R$ and a left image $246_L$ of object 230, on a rear image plane (not shown) of optical relay assembly $228_2$, according to light beams 240D and 242D, respectively. There is the same disparity δ between right image $246_R$ and left image $246_L$. During an optical relaying process, optical relay assembly array 212 produces a plurality of right intermediate images and left intermediate images, such as right intermediate image $252_R$ and left intermediate image $252_L$.

Optical assembly 214 projects a light beam 240E respective of right image $246_R$, and a light beam 242E respective of left image $246_L$, on lenticular lens layer 216. Lenticular lens layer 216 projects light beams 240E and 242E, on adjacent cells $248_R$ and $248_L$, respectively, of light sensor array 218. Processor 236 produces a video output respective of the right view and left view of object 230, according to an output of light sensor array 218, as described herein below in connection with FIGS. 6A, and 6B, for display 238 to display a right image and a left image of object 230. A user (not shown) can perceive a stereoscopic sensation of object 230, by viewing display 238 via a viewing device (not shown), such as a stereoscopic pair of spectacles, and the like.

It is noted that since $d_2 < d_1$, optical relay assembly array 212 can be of a substantially small gage, which allows elongated endoscopic housing 202 to have a substantially small diameter (i.e., low gage). This substantially low gage of optical relay assembly array 212 allows usage of a plurality of optical relay assemblies, each having a substantially small diameter. This substantially low gage of optical relay assembly array 212, furthermore allows usage of an optical relay assembly array having a substantially small power to produce the right intermediate images and the left intermediate images. This substantially low gage of optical relay assembly array 212, furthermore improves the relaying process and the performance of optical relay assembly array 212, and reduces the weight thereof, and thus the overall weight of endoscope 200.

Furthermore, by utilizing the substantially large volume of proximal end 222 of endoscope 200 for light sensor array 218, allows light sensor array 218 to include a substantially large number of cells, which in turn allows processor 236 to produce a stereoscopic image having a substantially high resolution. It is further noted that usage of a pair of right periscopic prism 204 and left periscopic prism 206, at an enlarged value of IPD (i.e., $d_1$), provides a substantially large value of disparity δ between right image $246_R$ and left image $246_L$, thereby enhancing the stereoscopic sensation of the image of object 230, which the user perceives by viewing display 238.

It is noted that IPD transformer 250 receives light beams 240A and 242A at an IPD which is substantially larger than the one that each of optical relay assemblies $228_1$ and $228_2$, is capable to receive light beams at, without employing IPD transformer 250. This provision allows usage of lenses (not shown) in each of optical relay assemblies $228_1$ and $228_2$, of a diameter φ, smaller than that of an endoscope which is devoid of such an IPD transformer. This provision further reduces the value of a term $φ^2/L$, where φ is the diameter of the lens, and L is the distance between each consecutive image plane respective of optical relay assembly array 212 (e.g., right image 244R and left image 244L on one hand, and right intermediate image 252R and left intermediate image 252L on the other hand), at substantially the same value of the introversion angle α.

Figure 5A:
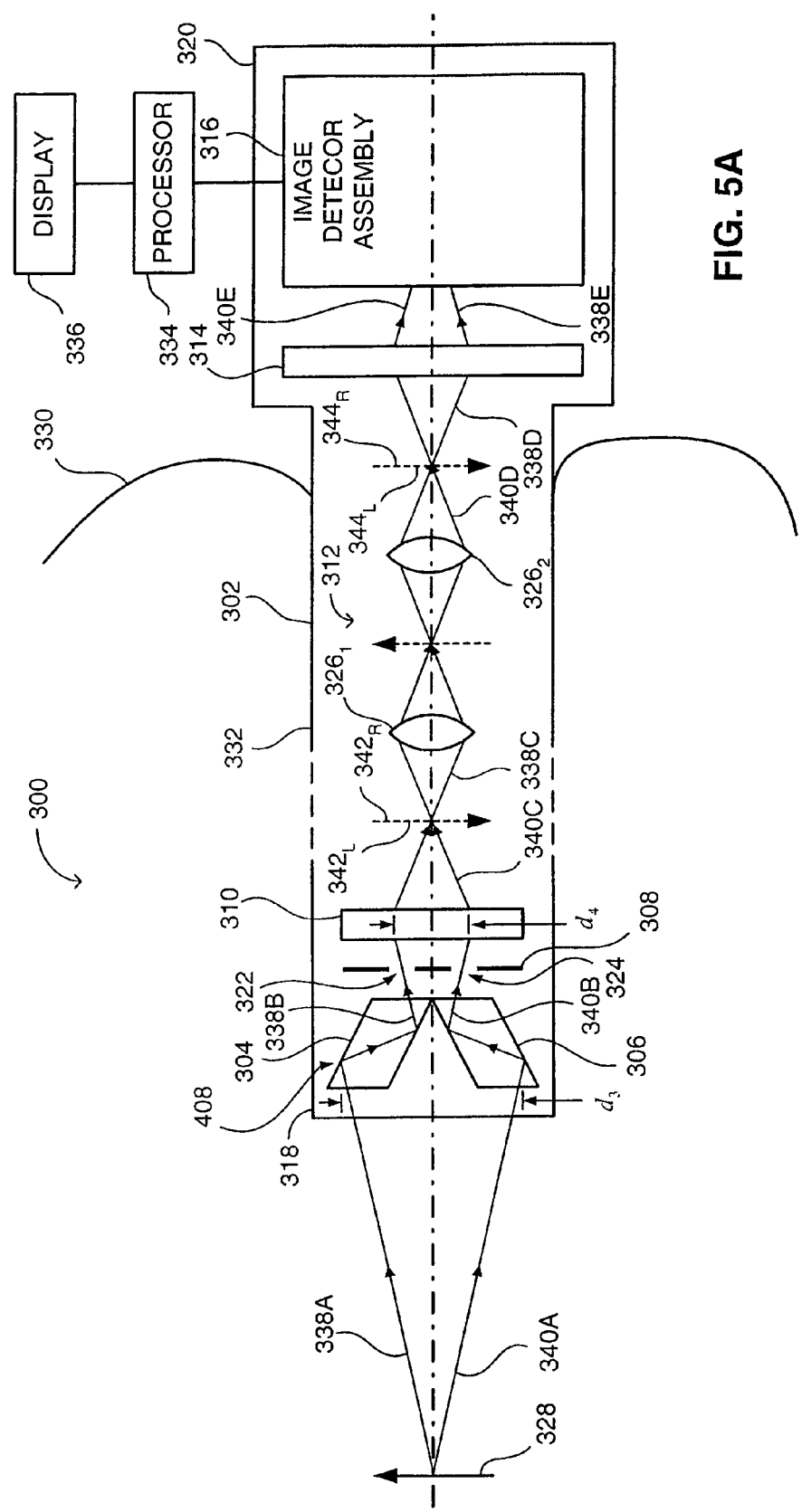
FIG. 5A is a schematic illustration of an endoscope, constructed and operative according to another embodiment of the disclosed technique.
Figure 5B:
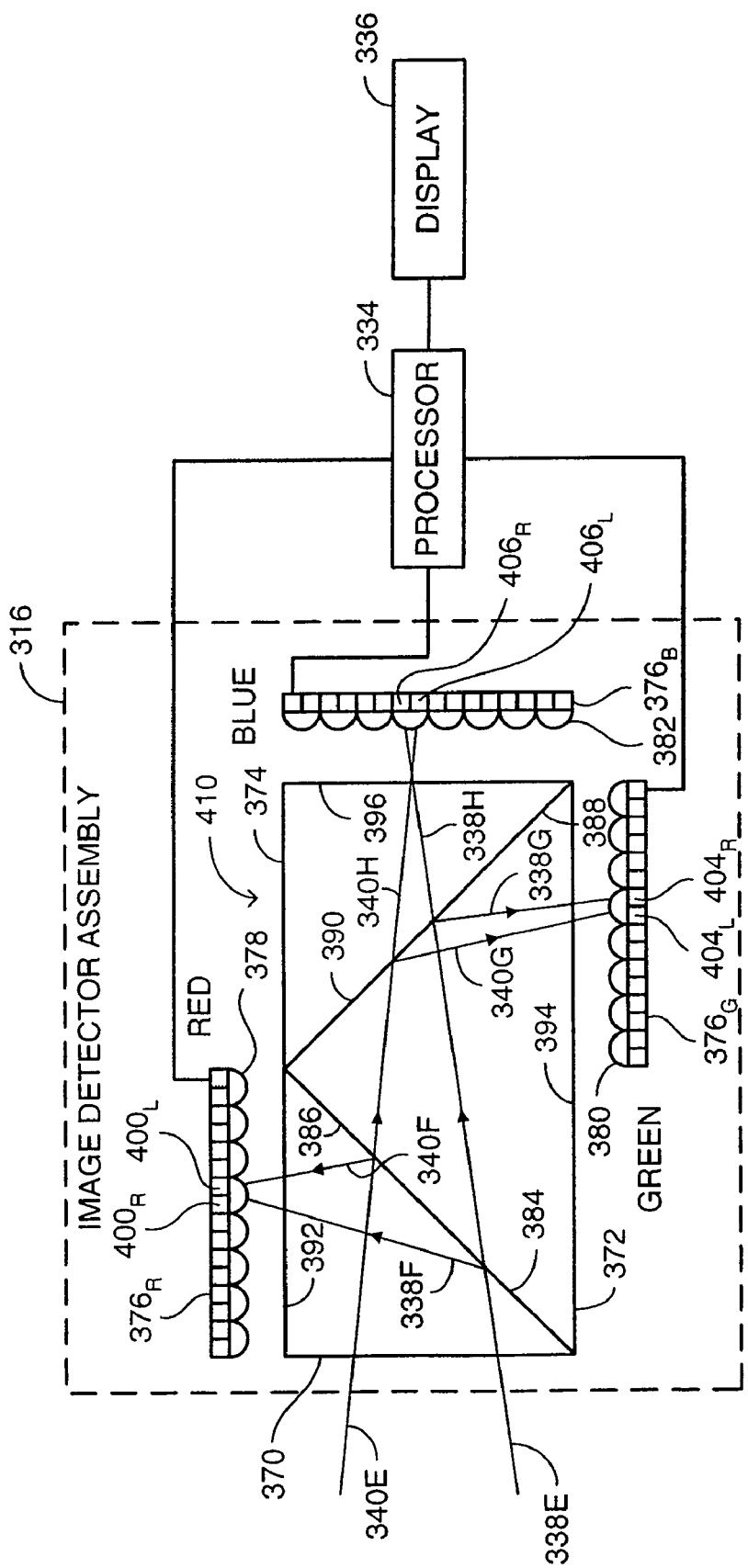
FIG. 5B is a schematic illustration of the image detector assembly of the endoscope of FIG. 5A.

Reference is now made to FIGS. 5A, and 5B. FIG. 5A is a schematic illustration of an endoscope generally referenced 300, constructed and operative according to another embodiment of the disclosed technique. FIG. 5B is a schematic illustration of the image detector assembly of the endoscope of FIG. 5A.

With reference to FIG. 5A, endoscope 300 includes an elongated endoscopic housing 302, an IPD transformer 408, an aperture stop 308, an objective 310, an optical relay assembly array 312, an optical assembly 314, and an image detector assembly 316. Elongated endoscopic housing 302 includes a distal end 318 and a proximal end 320. IPD transformer 408 includes a right periscopic prism 304 and a left periscopic prism 306. Aperture stop 308 includes a right pupil 322 and a left pupil 324. Optical relay assembly array 312 includes a plurality of optical relay assemblies $326_1$ and $326_2$.

An object 328 is located within a cavity 330 of the body of a patient (not shown). Right periscopic prism 304, left periscopic prism 306, aperture stop 308, and objective 310 are located at distal end 318. Optical assembly 314, and image detector assembly 316 are located at proximal end 320. Optical relay assembly array 312 is located in a midsection 332 of elongated endoscopic housing 302, between distal end 318 and proximal end 320. A processor 334 is coupled with image detector assembly 316, and with a display 336.

Right periscopic prism 304 receives a light beam 338A respective of a right view of object 328. Left periscopic prism 306 receives a light beam 340A respective of a left view of object 328. An IPD respective of the pair of right periscopic prism 304 and left periscopic prism 306 is designated by $d_3$. Right periscopic prism 304 reflects light beam 338A toward objective 310, as a light beam 338B, via right pupil 322. Left periscopic prism 306 reflects light beam 340A toward objective 310, as a light beam 340B, via left pupil 324. An IPD respective of right pupil 322 and left pupil 324 is designated by $d_4$, where $d_4 < d_3$.

Objective 310 projects a right image $342_R$ and a left image $342_L$ of object 328, according to light beams 338C and 340C, respectively, on a front image plane (not shown) of optical relay assembly $326_1$. Optical relay assembly array 312 transmits light beams 338C and 340C there through, in a multiple manner, to project a right image $344_R$ and a left image $344_L$ of object 328, on a rear image plane (not shown) of optical relay assembly $326_2$, according to light beams 338D and 340D, respectively. Optical assembly 314 projects light beams 338D and 340D as light beams 338E and 340E, on image detector assembly 316.

With reference to FIG. 5B, image detector assembly 316 includes a light director 410, three light sensor arrays $376_R$, $376_G$, and $376_B$, and three lenticular lens layers 378, 380, and 382. Light director 410 is an optical device which separates each of light beams 338E and 340E, according to a plurality of predetermined ranges of wavelengths, and directs these separated light beams in predetermined directions toward predetermined lenticular elements of each of lenticular lens layers 378, 380, and 382, as described herein below. For this purpose, light director 410 can include three prisms 370, 372, and 374, wherein the surface of each of prisms 370, 372, and 374 which are in mutual contact, is coated by a plurality of layers of a dichroic substance, each dichroic substance having a selected index of refraction, and being applied at a selected thickness. Light sensor array $376_R$ detects an image (not shown) in a red range of wavelengths. Light sensor array 376 detects the image in a green range of wavelengths. Light sensor array $376_B$ detects the image in a blue range of wavelengths.

A first surface 384 of prism 372 makes contact with a surface 386 of prism 370. A second surface 388 of prism 372 makes contact with a surface 390 of prism 374. Light sensor array $376_R$ is located behind a surface 392 of prism 370. Light sensor array $376_G$ is located behind a surface 394 of prism 372. Light sensor array $376_B$ is located behind a surface 396 of prism 374. Lenticular lens layers 378, 380, and 382 are located in front of light sensor arrays $376_R$, $376_G$, and $376_B$, respectively. Processor 334 is coupled with light sensor arrays $376_R$, $376_G$, and $376_e$.

Surface 386 reflects a portion of light beam 340E, toward lenticular lens layer 378, as a light beam 340F. Lenticular lens layer 378 projects light beam 340F on a cell $400_R$ of light sensor array $376_R$. Surface 386 reflects a portion of a light beam 338E, toward lenticular lens layer 378, as a light beam 338F. Lenticular lens layer 378 projects light beam 338F on a cell $400_L$ of light sensor array $376_R$.

Surface 388 reflects another portion of light beam 340E, toward lenticular lens layer 380, as a light beam 340G. Lenticular lens layer 380 projects light beam 340G on a cell $404_R$ of light sensor array 376. Surface 388 reflects another portion of light beam 338E, toward lenticular lens layer 380, as a light beam 338G. Lenticular lens layer 380 projects light beam 338G on a cell $404_L$ of light sensor array 376.

Surfaces 384 and 388 transmit another portion of light beam 340E, toward lenticular lens layer 382, as a light beam 340H. Lenticular lens layer 382 projects light beam 340H on a cell $406_R$ of light sensor array $376_B$. Surfaces 384 and 388 transmit another portion of light beam 338E, toward lenticular lens layer 382, as a light beam 338H. Lenticular lens layer 382 projects light beam 338H on a cell $406_L$ of light sensor array $376_B$. In this manner, light sensor arrays $376_R$, $376_G$, and $376_B$, detect an image (not shown) of object 328, in a red, green, and blue range of wavelengths, respectively.

Alternatively, image detector assembly 316 can include only two selective surfaces such as surfaces 386 and 390, each having such characteristics that light sensor arrays $376_R$, $376_G$, and $376_B$, detect the image of object 328, in the red, green, and blue range of wavelengths, respectively, as described herein above. In this case, the prisms can be eliminated from the image detector assembly.

Processor 334 produces a color video output respective of the right view and left view of object 328, according to outputs of image detector assembly 316, for display 336 to display a right color image and a left color image of object 328. A user can perceive a stereoscopic sensation of object 328, in color, by viewing display 336 via a viewing device (not shown), such as a stereoscopic pair of spectacles, and the like.

It is noted that since $d_4<d_3$, optical relay assembly array 312 (FIG. 5A) can be of a substantially small gage, which allows elongated endoscopic housing 302 to have a substantially small diameter (i.e., low gage). This substantially low gage of optical relay assembly array 312 reduces allows usage of a plurality of optical relay assemblies, each having a substantially small diameter. This substantially low gage of optical relay assembly array 312, furthermore allows usage of an optical relay assembly array having a substantially small power to produce the right intermediate images and the left intermediate images. This substantially low gage of optical relay assembly array 312, furthermore improves the relaying process and the performance of optical relay assembly array 312, and reduces the weight thereof, and thus the overall weight of endoscope 300.

Furthermore, by utilizing the substantially large volume of proximal end 320 of endoscope 300 for image detector assembly 316, allows each of light sensor arrays $376_R$, $376_G$, and $376_B$, to include a substantially large number of cells, which in turn allows processor 334 to produce a stereoscopic image having a substantially high resolution.

Figure 6A:
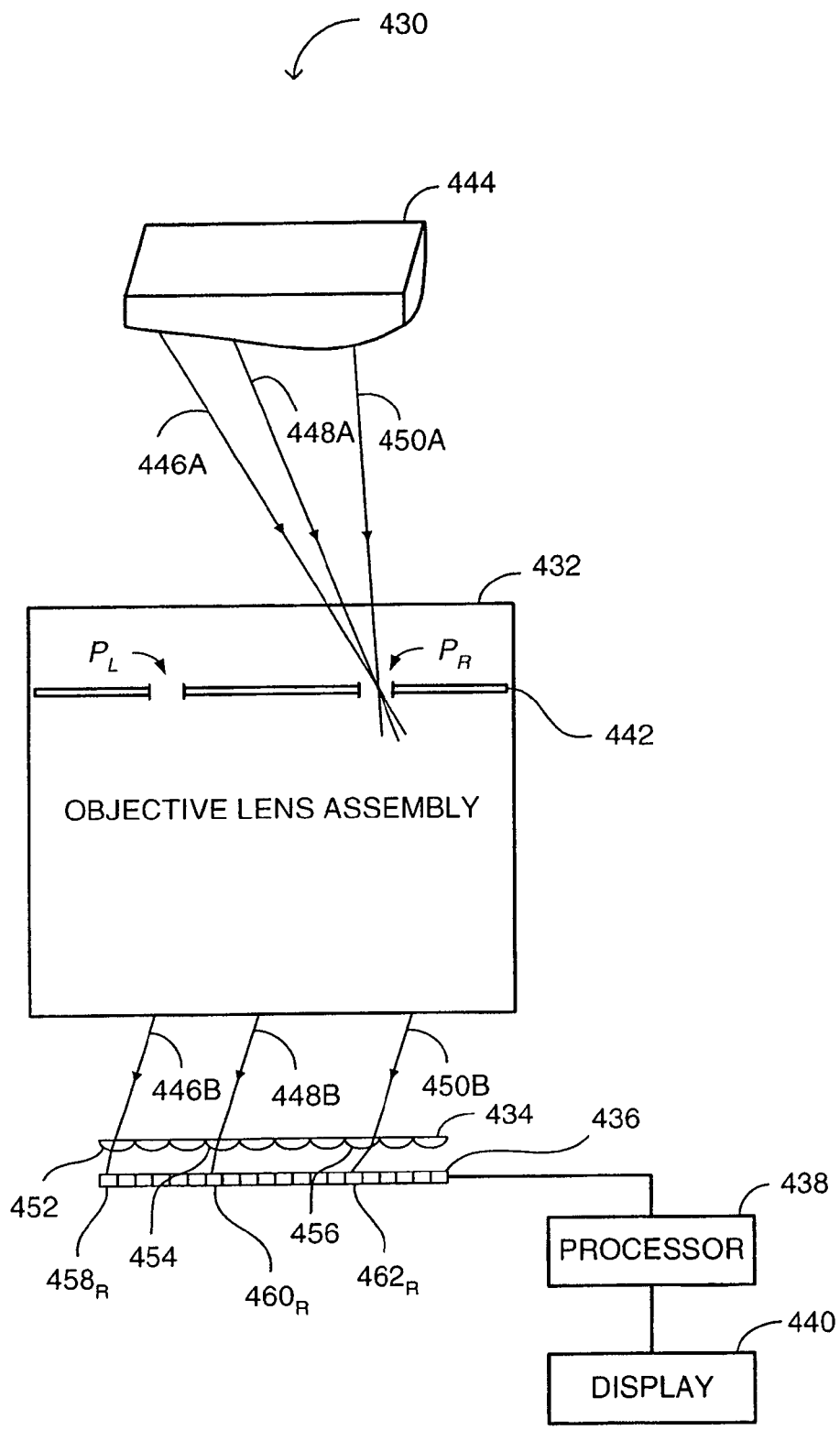
FIG. 6A is a schematic illustration of a stereoscopic imaging apparatus, constructed and operative according to a further embodiment of the disclosed technique.
Figure 6B:
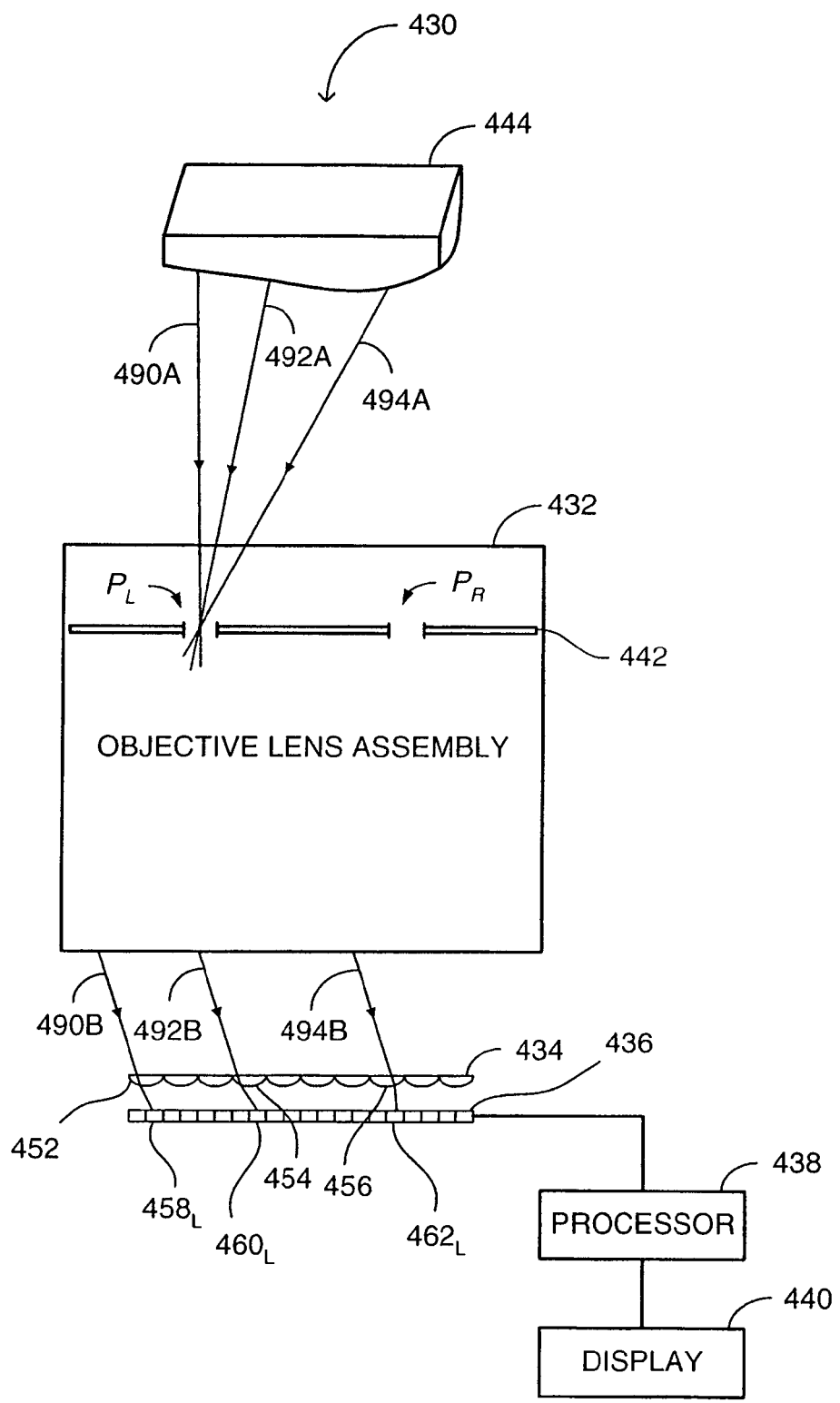
FIG. 6B is a schematic illustration of the stereoscopic imaging apparatus of FIG. 6A, with a different set of light beams.

Reference is now made to FIGS. 6A, and 6B. FIG. 6A is a schematic illustration of a stereoscopic imaging apparatus generally referenced 430, constructed and operative according to a further embodiment of the disclosed technique. FIG. 6B is a schematic illustration of the stereoscopic imaging apparatus of FIG. 6A, with a different set of light beams.

With reference to FIG. 6A, stereoscopic imaging apparatus 430 includes an objective lens assembly 432, a lenticular lens layer 434, a light sensor array 436 (e.g., two-dimensional), a processor 438, and a display 440. Objective lens assembly 432 includes an aperture stop 442. Aperture stop 442 includes a right pupil $P_R$ and a left pupil $P_L$. Aperture stop 442 is located at a front focal plane (not shown) of objective lens assembly 432. Objective lens assembly 432 is a telecentric lens assembly on the image side thereof. Telecentric lens assembly is a lens assembly in which the size of an image of an object projected thereby on an image plane, remains constant, no matter how far the object is from the telecentric lens assembly. Furthermore, light beams which exit objective lens assembly 432 are substantially parallel. This is due to the fact that each of right pupil $P_R$ and left pupil $P_L$, are located on an object side of objective lens assembly 432. Aperture stop 442 transmits light incident upon right pupil $P_R$ and left pupil $P_L$, and substantially reflects or absorbs all other incident light.

Objective lens assembly 432 is located between an object 444 and lenticular lens layer 434. Lenticular lens layer 434 is located between objective lens assembly 432 and light sensor array 436. Processor 438 is coupled with light sensor array 436 and with display 440.

Light beams 446A, 448A, and 450A (i.e., chief rays), respective of a right view of object 444 enter right pupil $P_R$ through a center thereof. Objective lens assembly 432 projects light beams 446B, 448B, and 450B respective of light beams 446A, 448A, and 450A, respectively, on lenticular lenses 452, 454, and 456 of lenticular lens layer 434, respectively. Light beams 446B, 448B, and 450B are substantially mutually parallel. Lenticular lenses 452, 454, and 456, direct light beams 446B, 448B, and 450B toward cells 458$_R$, 460$_R$, and 462$_R$, respectively, of light sensor array 436.

With reference to FIG. 6B, light beams 490A, 492A, and 494A (i.e., chief rays), respective of a left view of object 444 enter left pupil P$_L$ through a center thereof. Objective lens assembly 432 projects light beams 490B, 492B, and 494B respective of light beams 490A, 492A, and 494A, respectively, on lenticular lenses 452, 454, and 456 of lenticular lens layer 434, respectively. Light beams 490B, 492B, and 494B are substantially mutually parallel. Lenticular lenses 452, 454, and 456, direct light beams 490B, 492B, and 494B toward cells 458, 460, and 462, respectively, of light sensor array 436.

Processor 438 produces a video output respective of the right view and left view of object 444, according to an output of light sensor array 436, for display 440 to display a right image and a left image of object 444. A user can perceive a stereoscopic sensation of object 444, by viewing display 440 via a stereoscopic pair of spectacles (not shown).

Alternatively, the objective lens assembly can be a non-telecentric lens assembly in which the light beams which exit the objective lens assembly are non-parallel. In this case, the objective lens assembly directs each of the light beams respective of the right view of the object and the left view of the object, toward predetermined lenticular lenses of the lenticular lens layer, and each lenticular lens directs the respective light beam toward a predetermined cell of the light sensor array.

According to the present embodiment, right pupil P$_L$ and left pupil P$_R$ define the "eyes" of stereoscopic imaging apparatus 430, which are required for stereoscopic imaging. It is noted that the light beams arrive at the lenticular lenses substantially in one of two specific directions. Hence, each lenticular lens distinguishes precisely between the light received from right pupil P$_R$ and that received from left pupil P$_L$. It is further noted that the difference between the direction of light beams 446B, 448B, and 450B on one hand, and that of light beams 490B, 492B, and 494B, on the other hand, depends on the location of right pupil P$_R$ and left pupil P$_L$, relative to objective lens assembly 432, along an optical axis (not shown) of stereoscopic imaging apparatus 430.

It will be appreciated by persons skilled in the art that the disclosed technique is not limited to what has been particularly shown and described hereinabove. Rather the scope of the disclosed technique is defined only by the claims, which follow.

The invention claimed is:

1. Stereoscopic endoscope comprising:
   an elongated endoscopic housing;
   an interpupilar distance (IPD) transformer located at a distal end of said elongated endoscopic housing and behind an object, said IPD transformer receiving light beams respective of a right view and a left view of said object, at a substantially large IPD;
   an objective located behind said IPD transformer, said objective receiving said light beams from said IPD transformer, said objective projecting a distal right view image and a distal left view image of said object on a distal image plane, said distal image plane being located in the vicinity of said distal end;
   an optical relay assembly array located behind said objective, said objective optically coupled with said optical relay assembly array, said optical relay assembly array comprising a plurality of serially located optical relay assemblies, said optical relay assemblies sequentially relaying said distal right view image and said distal left view image, a proximal optical relay assembly of said optical relay assembly array located at a proximal end of said elongated endoscopic housing, projecting a relayed right view image and a relayed left view image of said object, on a proximal image plane located at said proximal end;
   a light sensor array located behind said optical relay assembly array, said light sensor array including a plurality of light sensors;
   a lenticular lens layer located in front of said light sensor array, said lenticular lens layer including a plurality of lenticular elements, each of said lenticular elements being located in front of a selected two-dimensional group of said light sensors; and
   an optical assembly located in front of said lenticular lens layer, said optical assembly transmitting a relayed right view light beam according to said relayed right view image, and a relayed left view light beam according to said relayed left view image, to a respective one of said lenticular elements, said respective lenticular element transmitting said relayed right view light beam and said relayed left view light beam, to respective ones of said selected group of said light sensors, to enable respective ones of said selected group of said light sensors, to produce a sensor output respective of said relayed right view light beam and said relayed left view light beam.

2. The stereoscopic endoscope according to claim 1, further comprising:
   a right pupil for transmitting a distal right view light beams respective of said distal right view image there through, toward said objective; and
   a left pupil for transmitting a distal left view light beams respective of said distal left view image there through, toward said objective.

3. The stereoscopic endoscope according to claim 1, further comprising:
   a processor coupled with said light sensor array, said processor producing a video output respective of said right view and said left view, according to said sensor output; and
   a display coupled with said processor, said display displaying a visible right view image and a visible left view image of said object, according to said video output.

4. The stereoscopic endoscope according to claim 1, wherein said IPD transformer comprises:
   a right periscopic prism for receiving a right view distal light beam respective of said right view of said object, at a right entrance point, said right periscopic prism reflecting said right view distal light beam twice, toward said objective, at a right exit point; and
   a left periscopic prism for receiving a left view distal light beam respective of said left view of said object, at a left entrance point, said left periscopic prism reflecting said left view distal light beam twice, toward said objective, at a left exit point,
   wherein an entrance distance between said right entrance point and said left entrance point, is greater than an exit distance between said right exit point and said left exit point.

5. The stereoscopic endoscope according to claim 1, wherein said elongated endoscopic housing is made of a rigid material.

6. The stereoscopic endoscope according to claim 1, wherein said elongated endoscopic housing is flexible.

7. Stereoscopic endoscope comprising:

an elongated endoscopic housing;

an interpupilar distance (IPD) transformer located at a distal end of said elongated endoscopic housing and behind an object, said IPD transformer receiving light beams respective of a right view and a left view of said object, at a substantially large IPD;

an objective located behind said IPD transformer, said objective receiving said light beams from said IPD transformer, said objective projecting a distal right view image and a distal left view image of said object on a distal image plane, said distal image plane being located at said distal end;

an optical relay assembly array located behind said objective, said optical relay assembly array comprising a plurality of serially located optical relay assemblies, said optical relay assemblies sequentially relaying said distal right view image and said distal left view image, a proximal optical relay assembly of said optical relay assembly array located at a proximal end of said elongated endoscopic housing, projecting a relayed right view image and a relayed left view image of said object, on a proximal image plane located at said proximal end;

a light detector assembly located behind said optical relay assembly array, said light detector assembly comprising:
  a set of three light sensor arrays, each of said set of three light sensor arrays being optically coupled with said optical relay assembly array, each of said set of three light sensor arrays including a plurality of light sensors;
  a set of three lenticular lens layers, each of said set of three lenticular lens layers being located in front of a respective one of said set of three light sensor arrays, each of said set of three lenticular lens layers including a plurality of lenticular elements, each of said lenticular elements being located in front of a respective two-dimensional group of said light sensors of said respective light sensor array; and
  a light director optically coupled with said optical relay assembly array and with said set of three lenticular lens layers, said light director directing incoming light to predetermined directions, in predetermined ranges of wavelengths, toward predetermined lenticular elements of each lenticular lens layer of said set of three lenticular lens layers; and an optical assembly located between said optical relay assembly array and said light director, said optical assembly transmitting a relayed right view light beam according to said relayed right view image, and a relayed left view light beam according to said relayed left view image, to said light director, said light director directing each of said relayed right view light beam and said relayed left view light beam, toward each of said predetermined lenticular elements, each of said predetermined lenticular elements transmitting said relayed right view light beam and said relayed left view light beam, to said respective group of said light sensors, to enable said respective group of each of said set of three light sensor arrays, to produce a corresponding sensor output respective of said relayed right view light beam and said relayed left view light beam.

8. The stereoscopic endoscope according to claim 7, further comprising:
  a right pupil for transmitting a distal right view light beam respective of said distal right view image there through, toward said objective; and
  a left pupil for transmitting a distal left view light beam respective of said distal left view image there through, toward said objective.

9. The stereoscopic endoscope according to claim 7, further comprising:
  a processor coupled with each of said set of three light sensor arrays, said processor producing a video output respective of said right view and said left view, according to said respective sensor output; and
  a display coupled with said processor, said display displaying a visible right view image and a visible left view image of said object, according to said video output.

10. The stereoscopic endoscope according to claim 7, wherein said IPD transformer comprises:
  a right periscopic prism for receiving a right view distal light beam respective of said right view of said object, at a right entrance point, said right periscopic prism reflecting said right view distal light beam twice, toward said objective, at a right exit point; and
  a left periscopic prism for receiving a left view distal light beam respective of said left view of said object, at a left entrance point, said left periscopic prism reflecting said left view distal light beam twice, toward said objective, at a left exit point,
  wherein an entrance distance between said right entrance point and said left entrance point, is greater than an exit distance between said right exit point and said left exit point.

11. The stereoscopic endoscope according to claim 7, wherein said elongated endoscopic housing is made of a rigid material.

12. The stereoscopic endoscope according to claim 7, wherein said elongated endoscopic housing is flexible.

13. The stereoscopic endoscope according to claim 7, wherein said light director comprises:
  a first selective surface reflecting said relayed right view light beam within a first range of wavelengths, detectable by a first one of said set of three light sensor arrays, toward a first one of said set of three lenticular lens layers, in a first direction, said first selective surface reflecting said relayed left view light beam within said first range of wavelengths, toward said first lenticular lens layer, in a second direction; and
  a second selective surface receiving a first right view light beam remainder of said relayed right view light beam, and a first left view light beam remainder of said relayed left view light beam, from said first selective surface, said second selective surface reflecting said first right view light beam remainder, within a second range of wavelengths, detectable by a second one of said set of three light sensor arrays, toward a second one of said set of three lenticular lens layers, in a third direction, said second selective surface reflecting said left view light beam remainder, within said second range of wavelengths, toward said second lenticular lens layer, in a fourth direction, said second selective surface transmitting a second right view light beam remainder of said first right view light beam remainder, within a third range of wavelengths, detectable by a third one of said set of three light sensor arrays, toward a third one of said set of three lenticular lens layers, in a first original direction, and a second left view light beam remainder of said first left view light beam remainder, within said third range of wavelengths, toward said third lenticular lens layers, in a second original direction.

14. The stereoscopic endoscope according to claim 13, wherein said first selective surface is a surface shared by a first prism and a second prism, and
wherein said second selective surface is another surface shared by said second prism and a third prism.

* * * * *